(12) United States Patent
McNair

(10) Patent No.: US 11,335,461 B1
(45) Date of Patent: May 17, 2022

(54) PREDICTING GLYCOGEN STORAGE DISEASES (POMPE DISEASE) AND DECISION SUPPORT

(71) Applicant: CERNER INNOVATION, INC., Kansas City, KS (US)

(72) Inventor: Douglas S. McNair, Leawood, KS (US)

(73) Assignee: CERNER INNOVATION, INC., North Kansas City, MO (US)

( * ) Notice: Subject to any disclaimer, the term of this patent is extended or adjusted under 35 U.S.C. 154(b) by 334 days.

(21) Appl. No.: 15/913,663

(22) Filed: Mar. 6, 2018

Related U.S. Application Data

(60) Provisional application No. 62/467,786, filed on Mar. 6, 2017.

(51) Int. Cl.
*G16H 50/20* (2018.01)
*G06N 20/00* (2019.01)
*G16B 40/00* (2019.01)

(52) U.S. Cl.
CPC ............. *G16H 50/20* (2018.01); *G06N 20/00* (2019.01); *G16B 40/00* (2019.02)

(58) Field of Classification Search
CPC ......... G16H 50/20; G06N 20/00; G16B 40/00
USPC ............................................................ 705/2
See application file for complete search history.

(56) References Cited

U.S. PATENT DOCUMENTS

| | | | |
|---|---|---|---|
| 5,804,405 A | 9/1998 | Ahlfors | |
| 6,129,664 A | 10/2000 | Macfarlane et al. | |
| 6,759,189 B1 | 7/2004 | Meikle et al. | |
| 7,361,481 B2 | 4/2008 | Meikle et al. | |
| 7,378,231 B1 | 5/2008 | Meikle et al. | |
| 7,662,558 B2 | 2/2010 | Liew | |
| 7,951,545 B2 | 5/2011 | Okamura et al. | |
| 8,003,337 B2 | 8/2011 | Okamura et al. | |

(Continued)

FOREIGN PATENT DOCUMENTS

| | | |
|---|---|---|
| EP | 2024745 A2 | 2/2009 |
| JP | 2015-230199 A | 12/2015 |
| WO | 2016/012864 A2 | 1/2016 |

OTHER PUBLICATIONS

Aerts, J.M.F.G., Kallemeijn, W.W., Wegdam, W. et al. Biomarkers in the diagnosis of lysosomal storage disorders: proteins, lipids, and inhibodies. J Inherit Metab Dis 34, 605-619 (2011). https://doi.org/10.1007/s10545-011-9308-6 (Year: 2011).*

(Continued)

*Primary Examiner* — Michael Tomaszewski
*Assistant Examiner* — Rachael Sojin Stone
(74) *Attorney, Agent, or Firm* — Shook, Hardy & Bacon L.L.P.

(57) ABSTRACT

A diagnostic and decision support technology is provided for determining the presence, identity, and/or severity of an inherited lysosomal storage disorder. In particular, a mechanism is provided to detect and classify a lysosomal storage disorder in a human patient, which utilizes a logistic regression classifier determined based on a multi-variable-composite-biomarker comprising a specific set of physiological variables of the patient. This multi-variable statistical predictive biomarker approach may be employed for identifying persons whose attributes are consistent with features or glycogen storage diseases, such as late-onset Pompe disease.

20 Claims, 8 Drawing Sheets

(56) References Cited

U.S. PATENT DOCUMENTS

| | | | |
|---|---|---|---|
| 8,101,358 B2 | 1/2012 | Liew | |
| 8,232,073 B2 | 7/2012 | Crawford et al. | |
| 8,410,101 B2 | 4/2013 | Schiffmann et al. | |
| 8,569,001 B2 | 10/2013 | Okamura et al. | |
| 8,592,140 B2 | 11/2013 | Crawford et al. | |
| 8,771,974 B2 | 7/2014 | Crawford et al. | |
| 8,809,009 B2 | 8/2014 | Crawford et al. | |
| 9,222,120 B2 | 12/2015 | Crawford et al. | |
| 9,340,822 B2 | 5/2016 | Crawford et al. | |
| 9,495,514 B2 | 11/2016 | McNair | |
| 2006/0172429 A1* | 8/2006 | Nilsson | G01N 33/6851 436/71 |
| 2007/0077553 A1* | 4/2007 | Bentwich | C12Q 1/703 435/5 |
| 2007/0118410 A1* | 5/2007 | Nadai | G06Q 30/04 705/4 |
| 2008/0056994 A1 | 3/2008 | Kaneski et al. | |
| 2009/0299645 A1* | 12/2009 | Colby | C12Q 1/6883 702/19 |
| 2010/0047844 A1 | 2/2010 | Aerts | |
| 2010/0062948 A1 | 3/2010 | Kleinfeld et al. | |
| 2011/0093249 A1* | 4/2011 | Holmes | G16H 50/20 703/6 |
| 2011/0212090 A1* | 9/2011 | Pedersen | A61K 39/0011 424/133.1 |
| 2013/0287772 A1* | 10/2013 | Halbert | C12Q 1/6883 424/134.1 |
| 2013/0304392 A1* | 11/2013 | Deciu | G16B 20/00 702/20 |
| 2015/0005189 A1* | 1/2015 | Wong | G01N 33/68 506/9 |
| 2016/0178643 A1* | 6/2016 | Everett | G01N 33/6893 506/9 |
| 2018/0068083 A1* | 3/2018 | Cohen | G16H 50/30 |
| 2019/0086324 A1* | 3/2019 | Marrinucci | B01L 3/5085 |
| 2021/0110895 A1* | 4/2021 | Shriberg | G16H 50/30 |
| 2021/0319899 A1* | 10/2021 | Liu | G06K 9/6263 |
| 2021/0353224 A1* | 11/2021 | Etkin | G01R 33/4808 |
| 2021/0358594 A1* | 11/2021 | Mellem | G16H 10/20 |
| 2021/0383924 A1* | 12/2021 | Rajan | G01N 33/483 |

OTHER PUBLICATIONS

Berk et al., "Studies of Bilirubin Kinetics in Normal Adults", Journal of Clinical Investigation, vol. 48, 1969, pp. 2176-2190.

Bhutani et al., "Predictive Ability of a Predischarge Hour-Specific Serum Bilirubin for Subsequent Significant Hyperbilirubinemia in Healthy Term and Near-Term Newborns", Pediatrics, vol. 103, No. 1, Jan. 1999, pp. 6-14.

Bjerre et al., "Surveillance Extreme Hypebilirubinaemia in Denmark. A Method to Identify the Newborn Infants", Acta Paediatrica, vol. 97, 2008, pp. 1030-1034.

Boo et al., "Prediction of Severe Hyperbilirubinaemia Using the Bilicheck Transcutaneous Bilirubinometer", Journal of Pediatrics and Child Health, vol. 43, 2007, pp. 297-302.

Dennery et al., "Neonatal Blue-Light Phototherapy Could Increase the Risk of Dysplastic Nevus Development", Pediatrics, vol. 120, No. 1, 2007, pp. 247-248.

Dennery et al., "Neonatal Hyperbilirubinemia", The New England Journal of Medicine, vol. 334, No. 8, Feb. 2001, pp. 581-590.

Dennery, Phyllis A., "Pharmacological Interventions for the Treatment of Neonatal Jaundice", Seminars in Neonatology, vol. 7, 2002, pp. 111-119.

Facchini et al., "Follow-Up of Neonatal Jaundice in Term and Late Premature Newborns", Jornal de Pediatria, vol. 83, No. 4, 2007, pp. 313-318.

Gartner et al., "Jaundice and Breastfeeding", Pediatric Clinics of North America, vol. 48, No. 2, Apr. 2001, pp. 389-399.

Gillespie et al., "One Size Does Not Fit All: Interpreting Laboratoty Data in Pediatric Patients", AMIA 2003 Symposium Proceedings, 2003, p. 850.

Gloria-Bottini et al., "ADA Genetic Polymorphism and the Effect of Smoking on Neonatal Bilirubinemia and Developmental Parameters", Early Human Development, vol. 11, 2008, pp. 739-743.

Huang et al., "Risk Factors for Sever Hyperbilirubinemia in Neonates", Pediatric Research, vol. 56, No. 5, 2004, pp. 682-689.

Ivanciuc, Ovidiu, "Applications of Support Vector Machines in Chemistry", Reviews in Computational Chemistry, vol. 23, 2007, pp. 291-400.

Jangaard et al., "Outcomes in a Population of Healthy Term and Near-Term Infants With Serum Bilirubin Levels of >Or=325 Micromol/L (>Or=19 mg/dL) Who Were Born in Nova Scotia, Canada, Between 1994 and 2000", Pediatrics, vol. 122, No. 1, Jul. 2008, pp. 119-124.

Kaplan et al., "Evaluation of Discharge Management in the Prediction of Hyperbilirubinemia: The Jerusalem Experience", The Journal of Pediatrics, vol. 150, 2007, pp. 412-417.

Keren et al., "A Comparison of Alternative Risk-Assessment for Predicting Significant Neonatal Hyperbilirubinemia in Terms and Near-Term Infants", Pediatrics, vol. 121, No. 1, Jan. 2008, pp. e170-e179.

Kuzniewicz et al., "Risk Factors for Severe Hyperbilirubinemia Among Infants with Borderline Bilirubin Levels: A Nested Case-Control Study", The Journal of Pediatrics, vol. 153, 2008, pp. 234-240.

"Management of Hyperbilirubinemia in the Newborn Infant 35 or More Weeks of Gestation", Pediatrics, vol. 114, Jul. 2004, pp. 297-316.

Moerschel et al., "A Practical Approach to Neonatal Jaundice", American Family Physician, vol. 77, No. 9, May 2008, pp. 1255-1262.

Ostrow et al., "Phototherapy for Neonatal Jaundice", The New England Journal of Medicine, vol. 358, No. 23, 2008, pp. 2524-2525.

Petrone et al., "Early Hospital Discharge of the Healthy Term Neonate: The Italian Perspective", Minerva Pediatrica, vol. 60, No. 3, 2008, pp. 273-276.

Setia et al., "Neonatal Jaundice in Asian, White, and Mixed-Race Infants", Archives of Pediatrics and Adolescent Medicine, vol. 156, No. 3, Mar. 2002, pp. 276-279.

Shortland et al., "Understanding Neonatal Jaundice; U.K Practice and International Profile", The journal of the Royal Society for the Promotion of Health, vol. 128, No. 4, Jul. 2008, pp. 202-206.

Zanardo et al., "Cytokines in Human Clostrum and Neonatal Jaundice", Pediatric Research, vol. 62, No. 2, 2007, pp. 191-194.

Pre-interview First Office Action received for U.S. Appl. No. 16/151,217, dated Mar. 28, 2022, 5 pages.

Sharma et al., "Machine Learning Based Analytics of Micro-MRI Trabecular Bone Microarchitecture and Texture in Type 1 Gaucher Disease", Journal of Biomechanics 49.9, available online at: <https://pubmed.ncbi.nlm.nih.gov/27109052/>, Jun. 14, 2016, pp. 1961-1968.

\* cited by examiner

EXAMPLE APPLICATION USER INTERFACE

| | enter |
|---|---|
| Patient aged between 10 and 50 years... | |
| Myalgia? (Y/N) [ICD-9: 729.1, ICD-10: M79.1] | Y |
| Three or more of the listed comorbid conditions*? (Y/N) | Y |
| CK > 200 U/L? (Y/N) | Y |
| RDW > 14.0 um? (Y/N) | Y |
| RBC sedimentation rate > 10 mm/hr? (Y/N) | Y |
| AST > 40 U/L? (Y/N) | N |
| ALT > 45 U/L? (Y/N) | Y |
| ALT/AST ratio > 1.0? (Y/N) | Y |
| MCV < 82fL? (Y/N) | N |
| Anion gap > 15 mEq/L? (Y/N) | Y |
| T4 < 5.0 ug/dL -or- fT4 < 0.8 ng/dL -or- treated with levothyroxine? (Y/N) | Y |
| TSH > 10mU/L -or- treated with levothyroxine? (Y/N) | Y |

| evaluate | results |
|---|---|
| data complete? | Yes |
| Likelihood of myopathy meriting DBS and other testing... | High |

( 69% 330 ) ( 33% 332 to 91% 336 )

| ICD-9 | | ICD-10 | |
|---|---|---|---|
| 728.87 | | M62.81 | |
| 786.05 | | R06.0x | |
| 787.2x | | R13.xx | |
| 781.2x | | R26.xx | |
| 723.9 | | M43.8X2 | M53.9 |
| 401.xx | | I10.xx | |
| 429.3 | | I51.7 | |
| 276.2 | | E87.2 | |
| 327.23 | | G47.33 | |
| 486.xx | V12.61 | J18.xx | Z87.01 |
| 518.8x | | J96.xx | |
| 789.xx | | R10.xxx | |
| 787.91 | | R19.7 | |
| 787.3 | | R14.0-1 | |
| V46.3 | | Z99.3 | |

* Comorbid conditions
- Muscle weakness
- Dyspnea (including orthopnea)
- Dysphagia
- Abnormal gait
- Camptocormia / Bent Spine Syndrome / Neck extensor myopathy
- Hypertension
- Left ventricular hypertrophy
- Respiratory acidosis, chronic
- Sleep-disordered breathing / Obstructive sleep apnea
- Community-acquired pneumonia, recurrent
- Acute respiratory failure
- Abdominal pain
- Diarrhea, chronic
- Bloating
- Wheelchair dependency

*FIG. 3.*

```
###########################################################################

# Bayesian logistic regression model for small ICD-10 Pompe dataset

##################################################################### library(mcmc)

lopd <- read.csv(file="c:/0_cerdsm/0__math_models/genzyme/pompe/dsm_lopd10.csv",
header=TRUE,
        colClasses=c("character",rep("integer",12),"numeric","factor"))
# pat,myalg,comor,ck,rdw,sed,ast,alt,aarat,mcv,ag,t4,tsh,score,lopd
lopd <- lopd[,-1]

# conventional logistic regression does not converge for so small and near-singular a dataset
# fit <- glm(lopd ~ ., data=lopd, family=binomial(link=logit), epsilon=1e-4, maxit=100)
out <- glm(lopd ~ score, data=lopd, family=binomial(), x=TRUE)

x <- out$x
y <- out$y
lupost <- function(beta, x, y) {
  eta <- as.numeric(x %*% beta)
  logp <- ifelse(eta < 0, eta - log1p(exp(eta)), - log1p(exp(- eta)))
  logq <- ifelse(eta < 0, - log1p(exp(eta)), - eta - log1p(exp(- eta)))
  logl <- sum(logp[y == 1]) + sum(logq[y == 0])
  return(logl - sum(beta^2) / 8)
} set.seed(42)
beta.init <- as.numeric(coefficients(out))
out <- metrop(lupost, beta.init, 1e3, x=x, y=y)
out <- metrop(out, scale=0.7, x=x, y=y)
out$accept
out <- metrop(out, nbatch=1e4, x=x, y=y)
out$accept str(out)
List of 13
# $ accept    : num 0.192
# $ batch     : num [1:10000, 1:2] -5.24 -5.24 -5.24 -5.24 -5.24 ...
# $ initial   : num [1:2] -5.24 1.81
# $ final     : num [1:2] -6.22 2.03

# compare            -4.93 0.97
```

FIG. 5

```
library(pROC)

ds4 <- read.csv(file="c:/0_cerdsm/IP/orphan_pompe/roc.csv")
roc1 <- roc(ds4[,1] ~ ds4[,2], percent=TRUE,
# arguments for auc
# partial.auc=c(100, 90), partial.auc.correct=TRUE,
#  partial.auc.focus="sens",
# arguments for ci
  ci=TRUE, boot.n=100, ci.alpha=0.9, stratified=FALSE,
# arguments for plot
#  auc.polygon=TRUE, max.auc.polygon=TRUE,
  plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")

roc(ds4[,1] ~ ds4[,2], ds4, plot=TRUE)
```

FIG. 6

PREDICTING GLYCOGEN STORAGE DISEASES (POMPE DISEASE) AND DECISION SUPPORT

CROSS-REFERENCE TO RELATED APPLICATIONS

This application claims the benefit of U.S. Provisional Application No. 62/467,786; entitled "Predicting Glycogen Storage Diseases (Pompe Disease) and Decision Support," filed Mar. 6, 2017, which is expressly incorporated by reference in its entirety.

BACKGROUND

Lysosomal storage disorders are relatively rare inherited conditions involving enzyme deficiencies that can impair the functioning of many body organ systems by the accumulation of abnormal amounts of molecules in the lysosome organelles of the body's cells, usually producing severe disability and shortened life-expectancy. Effective treatments are available for some such disorders and may involve enzyme replacement therapy (ERT) involving ongoing periodic infusions of a synthetic recombinant version of the enzyme that is deficient, or stem cell transplantation, or other treatment modalities. Patients who have certain inherited lysosomal storage disorders, such as glycogen storage diseases, have widely varied clinical courses and presentations. Symptoms are typically first experienced in early childhood and can be misinterpreted by physicians and other clinicians. For example, in late-onset form of acid glucosidase deficiency (type II, Pompe disease), patients have fixed proximal muscle weakness and early respiratory insufficiency rather than exercise-induced symptoms. In other cases, such as debrancher deficiency (type III, Cori-Forbes disease), distal muscle weakness may be combined with cardiomyopathy and peripheral neuropathy in patients who in infancy had shown hepatomegaly, hypoglycemia, and failure to thrive—all of which may improve in later life. Signs and symptoms of the disease usually increase in number and severity as an individual ages. Variations in the presenting signs and symptoms are so diverse as to pose significant diagnostic challenges for most clinicians. The comparative rarity of glycogen storage diseases, such as late-onset Pompe Disease, means that most clinicians might never encounter a single patient having such a disorder in their entire clinical career. As a result, many patients having such conditions may go years undiagnosed or, alternatively, are mis-diagnosed and are treated for many years on the basis of an incorrect diagnosis. Such erroneous misdiagnosis-based treatments (or non-treatments) are ineffective or even unsafe and impair the health of the patient or lead to needless progression of the disease or irreversible loss of body function.

Pompe disease is an autosomal-recessive lysosomal storage disorder caused by alpha-1,4-glucosidase (GAA) enzyme deficiency. Prevalence ranges between 1:40,000 and 1:100,000. GAA dysfunction results in accumulation of large amounts of glycogen in skeletal and smooth muscle cells, hepatocytes, endothelial cells, and central nervous system neurons, interfering with the cells' functioning. GAA activity usually less than 1% is associated with early-infantile disease onset, and with cardiomyopathy, cardio-respiratory failure, and early death if enzyme replacement therapy (ERT) is not initiated. Partial reduction of GAA enzyme activity is associated with juvenile and adult late-onset Pompe disease (LOPD) onset, which is mainly characterized by progressive weakness of the limb girdle and axial muscles. In many instances, respiratory muscles are impaired early, and mechanical ventilatory support is indicated prior to wheelchair dependence in about 30% of LOPD patients. Affected respiratory muscles comprise the diaphragm in particular, but also the upper airway, and intercostal and abdominal muscles in severe disease, leading to recurrent pneumonia, respiratory acidosis, and other morbidities.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter. A diagnostic and decision support technology is provided for determining the presence, identity, and/or severity of an inherited lysosomal storage disorder. In particular, a mechanism is provided to detect and classify a lysosomal storage disorder in a human patient, which utilizes a logistic regression classifier determined based on a multi-variable composite-biomarker comprising a specific set of physiological variables of the patient. This multi-variable statistical predictive biomarker approach may be employed for identifying persons whose attributes are consistent with features of glycogen storage diseases, such as late-onset Pompe disease.

In embodiments, a multi-variable logistic regression statistical model capable of calculating a probability of a glycogen storage disease is generated. Using an input data set for a patient and the multi-variable logistic regression statistical model, a probability of a glycogen storage disease is determined and presented to a clinician to guide decision-making regarding additional diagnostic or prognostic evaluation. Moreover, some embodiments further comprise technologies for scoring or ascertaining the severity of a previously-diagnosed glycogen storage disease in human patients, such as late-onset Pompe disease, to assist in optimizing the medical treatment of individual patients and as a biomarker to follow the efficacy of treatment in animal models and in patients.

Based on this determined result (which may include one or more of a prediction, scoring, and/or severity), one or more actions may be carried out automatically or may be recommended, such as, without limitation, generating notifications such as electronic messages or alarms, based on said probability or score which may be emitted or otherwise provided to the caregiver and/or to the patient, advising them of the probability of an inherited glycogen storage disease meriting further diagnostic testing. In some embodiments, recommendations for specialist caregivers may be generated (or appointments may be automatically generated) and/or one or more EHR transactions may be automatically triggered by the determined result or score so as to initiate said diagnostic testing procedures. Some embodiments integrate with other decision support tools and related tools, such as Cerner Millennium orders, Discern Expert CDS, iView, or similar applications.

BRIEF DESCRIPTION OF THE DRAWINGS

The present technology is described in detail below with reference to the attached drawing figures, wherein:

FIG. 3 depicts an example graphical user interface of a multivariable predictive model component of a decision-support tool for predicting a glycogen storage disease in a human patient, in accordance with an embodiment of the disclosure;

FIG. 5 illustratively provides an example embodiment of a computer program routine for predicting a glycogen storage disease in accordance with an embodiment of this disclosure and further described in connection to FIGS. 2A and 2B; and FIG. 6 illustratively provides an example embodiment of a computer program routine for evaluating performance of an example embodiment reduced to practice and generating the ROC of FIG. 4A.

DETAILED DESCRIPTION

Figure 1A:
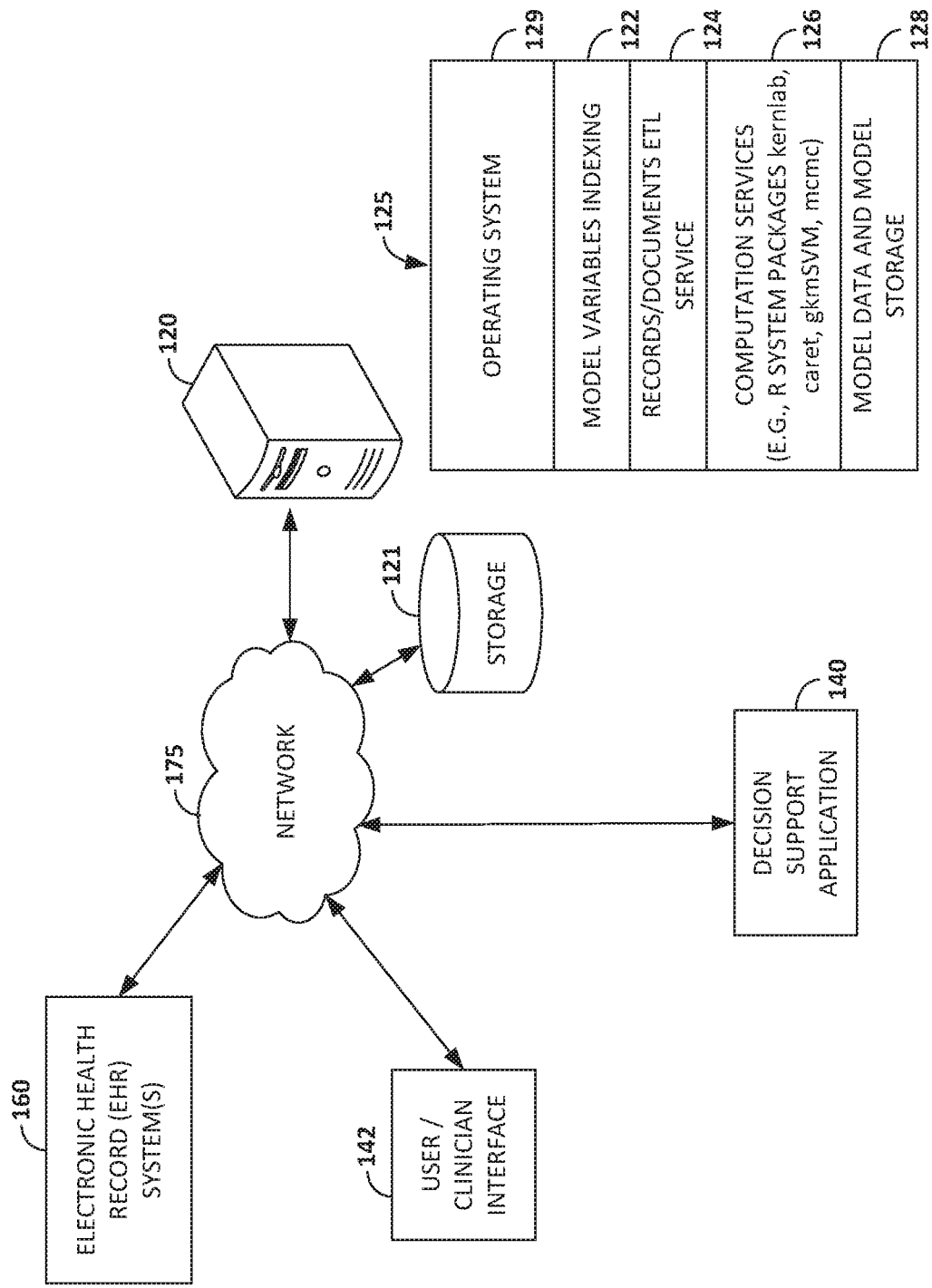
FIGS. 1A and 1B depict aspects of an illustrative architecture suitable for practicing an embodiment of the disclosure.

The subject matter of the present technology is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our disclosure may be embodied as, among other things: a method, system, or set of instructions embodied on one or more computer readable media. Accordingly, the embodiments may take the form of a hardware embodiment, a software embodiment, or an embodiment combining software and hardware. In one embodiment, the present disclosure takes the form of a computer-program product that includes computer-usable instructions embodied on one or more computer readable media.

Computer-readable media include both volatile and non-volatile media, removable and nonremovable media, and contemplate media readable by a database, a switch, and various other network devices. By way of example, and not limitation, computer-readable media comprise media implemented in any method or technology for storing information, including computer-storage media and communications media. Examples of stored information include computer-useable instructions, data structures, program modules, and other data representations. Computer storage media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, other magnetic storage devices, and other computer hardware or non-transitory storage devices. These technologies can store data momentarily, temporarily, or permanently.

Aspects of the technology described herein may be utilized for a screening procedure and multi-variable logistic regression based biomarker, which determines a numerical probability of a glycogen storage disease, such as late-onset Pompe disease. Such technology is particularly valuable for patients in whom other diagnostic and prognostic means tend to yield excessive false-negative results. In particular, we determined that increased red blood cell size distribution width (RDW), elevated aminotransferase enzyme levels often with increased alanine aminotransferase to aspartate aminotransferase ratio (ALT/AST) are strongly statistically associated with a diagnosis of late-onset Pompe disease. We have also determined that a tendency toward mild to moderate erythrocyte microcytosis, even in the absence of clinically significant anemia, may indicate increased destruction of RBCs in the reticuloendothelial system as part of the active processes in glycogen storage diseases. Likewise, laboratory indices of moderate hypothyroidism are further, novel correlates of increased likelihood or severity of a glycogen storage disease that are determined to have a statistically significant association for patients having a glycogen storage disease, such as late-onset Pompe disease. Utilizing our findings, which have not previously been reported in the known research literature, we developed a multi-variable composite biomarker pattern and predictive model, which we integrated into a decision-support system. In some embodiments, a decision support tool is provided, which may be a component in an electronic health records (EHR) system for detecting presence, identity, and/or severity of a glycogen storage disorder in patients, for notifying caregivers, and/or generating a recommendation or automatically performing additional actions such as scheduling diagnostic testing, treatments, modification to care plans, or other intervening actions. For example, cone embodiment comprises generating a notification indicating a patient's probability or severity of a glycogen storage disorder.

According to one embodiment, as will be further described herein, systems and computerized methods are provided for determining the presence, identity, and/or severity of a lysosomal storage disease or condition in an individual, where the disease or condition is associated with abnormal glycan or glycogen degradation or accumulation. In some embodiments, these systems or methods are incorporated into a decision support tool used for screening, monitoring, and/or treating a patient. The decision support tool may utilize a multi-variable composite biomarker pattern and predictive model. In one embodiment, the biomarker patterns comprise a set or pattern of physiological variables (which may also include clinical variables comprising conditions or clinical events) associated with a particular patient, which operate as independent variables in the model. In some embodiments, these physiological variables include: attribution of myalgia; attribution of a plurality (e.g., three or more) specific comorbid conditions;

elevated creatine kinase; increased red blood cell size distribution width (RDW; elevated aminotransferases; elevated alanine aminotransferase to aspartate aminotransferase ratio; erythrocyte microcytosis; increased anion gap; and/or laboratory indicia of hypothyroidism. In one embodiment, the specific comorbid conditions include: muscle weakness or sarcopenia; dyspnea or orthopnea; dysphagia; abnormal gait; camptocormia; hypertension; left ventricular hypertrophy; respiratory acidosis; sleep-disordered breathing or obstructive sleep apnea; recurrent community-acquired pneumonia; acute respiratory failure; abdominal pain; diarrhea; bloating; and/or wheelchair dependency as a composite variable.

Based on the multi-variable composite biomarker pattern, a predictive model and model coefficients are instantiated. A patient is identified and ERR information for the patient is accessed. The ERR information may include demographic, diagnostic, and laboratory information about the patient. Inputs for variable values corresponding to the biomarker pattern are received from the patient's ERR, and a probability is determined from the model. In some embodiments, the determined probability may be considered a score denoting the likelihood of the patient's having a glycogen storage disease or condition.

Next the determined probability or score is compared to one or more thresholds for glycogen storage disorder diagnostics. In some embodiments, based on the comparison, one or more risk levels are determined associated with the probability or severity of a glycogen storage disorder in the patient. Based on the comparison to the one or more thresholds, if the threshold(s) are not exceeded, then routine care for the patient may be carried out, as clinically indicated. But where the one or more thresholds are satisfied, then one or more intervening actions may be invoked. The one or more actions may be based on the determined probability or score satisfying the threshold(s) or the specific value of the determined probability or score. In some embodiments, an explanatory analysis may be prepared to accompany the model, for the significant values and deviations. Further, in some embodiments, an application and graphical user interface are provided for displaying a probability result or score denoting the likelihood of the patient's having a glycogen storage disease or condition.

As described above, due to the rarity of glycogen storage diseases, such as late-onset Pompe Disease, many clinicians might never encounter a single patient having such a disorder in their entire clinical career, which leads to many patients having such conditions may go years undiagnosed or may be mis-diagnosed. Such erroneous misdiagnosis-based treatments (or non-treatments) are ineffective or even unsafe and impair the health of the patient or lead to needless progression of the disease or irreversible loss of body function. In particular, conventional approaches to detecting this condition often entail measuring lysosomal enzyme levels or other specific gene products, or levels of glycogen-related compounds that result from the presence of or deficiencies in the enzyme activity of enzymes related to glycogen metabolism. Yet other conventional approaches entail genotyping or sequencing or other genomics or proteomics testing. Some of these methodologies involve, such as electromyography or tissue biopsy or other surgical procedures, and many of these conventional approaches are not widely available.

Moreover, these conventional approaches involve expensive, time-consuming tests and are therefore neither practical or suitable to utilize for the purposes of screening large numbers of prospective patients for possible lysosomal storage disorders. In contrast, embodiments of technology described herein solve these problems by providing a convenient, rapid, and inexpensive screening system and method that relies upon information that may already have been determined in the course of providing routine care and diagnostic testing or that, at most, requires limited additional measurements that are widely available in most health facilities. In some embodiments, based on our findings (discussed previously), the present technology can utilize information determined from routine diagnostic testing provided at various medical facilities and stored electronically. Thus, in some embodiments, the present technology provides for using information derived from multiple patients, over time, and at different healthcare facilities through ERR systems. Therefore, computer functionality is improved and advanced over conventional technologies, as the computer may now make predictions for a patient having a potential glycogen storage disease, which have less false-negative results than conventional methods of trying to diagnostically test each individual patient, which may or may not be initially performed on a patient based on the treating clinician's experience with such rare conditions. In some embodiments of the technology described herein, if the probability or risk of a glycogen storage disease or condition that is predicted by an embodiment of this technology exceeds a threshold, then electronic communication with the attending clinician may be generated and one or more EHR transactions may be initiated, such that diagnostic interventions (including more expensive, or time-consuming testing) capable of ruling-in or ruling-out the glycogen storage disease or condition are undertaken. Accordingly, embodiments of this technology may be utilized as a screening means to afford timely, accurate, and cost-effective definitive diagnosis in a substantially larger cohort of persons at-risk than has heretofore been practical.

Accordingly, in an example embodiment, a computerized method of initiating an intervention action for glycogen storage disease is provided. The method comprises: determining a multi-variable biomarker based on a set of physiological variables associated with an individual that is received as input data, the multi-variable biomarker comprising a plurality of: attribution of myalgia, attribution of a plurality of comorbid conditions, elevated creatine kinase, increased red blood cell size distribution width (RDW), elevated aminotransferases, elevated alanine aminotransferase to aspartate aminotransferase ratio, erythrocyte microcytosis, increased anion gap, or laboratory indicia of hypothyroidism; receiving a multi-variable logistic regression statistical model generated to determine a probability of a clinically significant glycogen storage disease; determining the probability of the clinically significant glycogen storage disease for the individual based on the multi-variable biomarker and the multi-variable logistic regression statistical model, wherein the multi-variable biomarker is used by the multi-variable logistic regression statistical model; and based on the probability of the clinically significant glycogen storage disease for the individual, initiating the intervention action, the intervention action comprising one or more of modifying treatment of the patient, ordering additional diagnostics for the patient, scheduling treatment or diagnostics for the patient, and issuing a notification to a caregiver associated with the patient.

In another example embodiment, one or more computer-readable storage devices storing computer-useable instructions that, when used by one or more computing devices, cause the one or more computing devices to perform a method of initiating an intervention action for glycogen storage disease. The method comprises: determining a multi-variable biomarker based on a set of physiological variables associated with an individual that is received as input data, the multi-variable biomarker comprising a plurality of: attribution of myalgia, attribution of a plurality of comorbid conditions, elevated creatine kinase, increased red blood cell size distribution width (RDW), elevated aminotransferases, elevated alanine aminotransferase to aspartate aminotransferase ratio, erythrocyte microcytosis, increased anion gap, or laboratory indicia of hypothyroidism; receiving a multi-variable logistic regression statistical model generated to determine a probability of a clinically significant glycogen storage disease; determining the probability of the clinically significant glycogen storage disease for the individual based on the multi-variable biomarker and the multi-variable logistic regression statistical model, wherein the multi-variable biomarker is used by the multi-variable logistic regression statistical model; and based on the probability of the clinically significant glycogen storage disease for the individual, initiating the intervention action, the intervention action comprising one or more of modifying treatment of the individual, ordering additional diagnostics for the individual, scheduling treatment or diagnostics for the individual, and issuing a notification to a caregiver.

In yet another example embodiment, one or more computer-readable storage devices storing computer-useable instructions that, when used by one or more computing devices, cause the one or more computing devices to perform a method of initiating an intervention action for glycogen storage disease. The method comprises: identifying an EMR associated with an individual; receiving a multi-variable logistic regression statistical model generated to determine a probability of a clinically significant glycogen storage disease; receiving input data from the EMR associated with the individual; determining a multi-variable biomarker based on a set of physiological variables in the received input data, the multi-variable biomarker comprising a plurality of: attribution of myalgia, attribution of a plurality of comorbid conditions, elevated creatine kinase, increased red blood cell size distribution width (RDW), elevated aminotransferases, elevated alanine aminotransferase to aspartate aminotransferase ratio, erythrocyte microcytosis, increased anion gap, or laboratory indicia of hypothyroidism; determining the probability of the clinically significant glycogen storage disease for the individual based on the multi-variable biomarker and the multi-variable logistic regression statistical model, wherein the multi-variable biomarker is used by the multi-variable logistic regression statistical model; and based on the probability of the clinically significant glycogen storage disease for the individual, initiating the intervention action, the intervention action comprising one or more of modifying treatment of the individual, ordering additional diagnostics for the individual, scheduling treatment or diagnostics for the individual, and issuing a notification to a caregiver.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the disclosure. Thus for readability, we show and reference items in the singular (while fully contemplating, where applicable, the plural).

As shown in FIG. 1, a block diagram is provided showing aspects of an example computing system architecture suitable for implementing an embodiment of this disclosure and designated generally as example operating environment 100. Example operating environment 100 provides an aspect of a computerized system for compiling and/or running aspects of this disclosure including collecting and analyzing unstructured text data from electronic health record(s), which may include claims data, to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Operating environment 100 is one example of a suitable environment and system architecture for implementing an embodiment of the disclosure. Other arrangements and elements can be used in addition to or instead of those shown, and some elements may be omitted altogether for the sake of clarity. Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example system 200, it is contemplated that in some embodiments functionality of these components can be shared or distributed across other components.

Environment 100 includes one or more electronic health record (ERR) systems, such as EHR system(s) 160 communicatively coupled to network 175, which is communicatively coupled to computer system 120. In some embodiments, components of environment 100 that are shown as distinct components may be embodied as part of or within other components of environment 100. For example, ERR system(s) 160 may comprise one or a plurality of ERR systems such as hospital EHR systems, health information exchange ERR systems, clinical genetics/genomics systems, ambulatory clinic ERR systems, psychiatry/neurology ERR systems, insurance, collections or claims records systems; and may be implemented in computer system 120. Similarly, ERR system 160 may perform functions for two or more of the ERR systems (not shown). In an embodiment, ERR system 160 includes historical claims data for health services, apportionment data, and related health services financial data.

In some embodiments of the technologies described herein, sequence itemset mining is performed using data about a population of patients derived from patient ERR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (ERR) system(s) 160 include one or more data stores of health-related records, which may be stored on storage 121, and may further include one or more computers or servers that facilitate the storing and retrieval of the health records. In some embodiments, ERR system(s) 160 and/or other records systems may be implemented as a cloud-based platform or may be distributed across multiple physical locations. EHR system(s) 160 may further include record systems, which store real-time or near real-time patient (or user) information, such as wearable sensor or monitor, bedside, or in-home patient monitors or sensors, for example.

Example operating environment 100 further includes a user/clinician interface 142 and decision support application 140, each communicatively coupled through network 175 to an EHR system 160. Although environment 100 depicts an indirect communicative coupling between interface 142 and application 140 with ERR system 160 through network 175, it is contemplated that an embodiment of interface 142 or application 140 are communicatively coupled to ERR system 160 directly. An embodiment of manager application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the technologies described herein, which may be used by a caregiver or screener to provide, for example, information about the likelihood of a specific patient or population of patients having a lysosomal storage disorder. In some embodiments, application 140 includes or is incorporated into a computerized decision support tool, as described herein. Further, some embodiments of application 140 utilize user/clinician interface 142.

In some embodiments, application 140 and/or interface 142 facilitates accessing and receiving information from a user or health care provider about a specific patient or set of patients, according to the embodiments presented herein. Embodiments of application 140 also may facilitate accessing and receiving information from a user or health care provider about a specific patient, caregiver, or population including historical data; health care resource data; variables measurements, timeseries, and predictions (including plotting or displaying the determined outcome and/or issuing an alert) described herein; or other health-related information, and facilitates the display of results, recommendations, or orders, for example. In an embodiment, application 140 also facilitates receiving orders, staffing scheduling, or queries from a user, based on the results of monitoring and/or forecasted outputs, which may in some embodiments utilize user interface 142. Decision-Support application 140 may also be used for providing diagnostic services or evaluation of the performance of various embodiments.

In some embodiments, user/clinician interface 142 may be used with application 140, such as described above. One embodiment of user/clinician interface 142 comprises a user interface that may be used to facilitate access by a user (including a clinician/caregiver such as a medical or psychiatric caregiver or the like) to a score or prediction determined according to the technologies described herein, including information indicating a likelihood that a patient has a lysosomal disorder, the severity of the disorder, and/or additional classification of the disorder, such as the likelihood of a specific condition (e.g., a glycogen storage disease condition such as late-onset Pompe disease.). One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application (which may take the form of an applet or app) or set of applications usable to manage user services provided by an embodiment of the technologies described herein.

In some embodiments, interface 142 may facilitate providing the output of the determined probability or score, recommendations, scheduling orders, providing instructions, or outputs of other actions described herein, as well as logging and/or receiving other feedback from the user/caregiver, in some embodiments. In an embodiment, interface 142 also facilitates receiving orders for the patient from the clinician/user, based on the results of monitoring and predictions. Interface 142 also may be used for providing diagnostic services or evaluation of the performance of various embodiments. One example embodiment of a user/clinician interface 142 and decision support application 140, which is actually reduced to practice is illustratively provided in FIG. 3, which is further described below.

Example operating environment 100 further includes computer system 120, which may take the form of one or more servers, and which is communicatively coupled through network 175 to ERR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, aspects of application 140 or interface 142 may operate on or utilize computer system 120. Similarly, a portion of computing system 120 may be embodied on user interface 142, application 140, and/or ERR system(s) 160. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local services or may be distributed across one or more components of operating environment 100, in the cloud, on one or more personal computers or servers such as system 120, and/or a computing device running interface 142 or application 140. In some embodiments, interface 142 and/or application 140 operate in conjunction with software stack 125.

In embodiments, model variables indexing service 122 and records/documents ETL service 124 provide services that facilitate retrieving patient physiological variables, which may include frequent item sets, extracting database records, and cleaning the values of variables in records. For example, services 122 and/or 124 may perform functions for synonymic discovery, indexing or mapping variables in records, or mapping disparate health systems' ontologies, such as determining that a particular medication frequency of a first record system is the same as another record system. In some embodiments, these services may invoke computation services 126.

Computation services 126 may perform statistical or computing operations, and may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages such as packages kernlab, for kernel-based machine learning classification, regression, clustering, and dimensionality reduction methods; caret, for training classification and regression models; gkmSVM, for implementing a Gapped-Kmer Support Vector Machine; and mcmc, for Markov Chain Monte Carlo operations. Computation services 126 also may include natural language processing services (not shown) such as Discern nCode™ developed by Cerner Corporation, or similar services. In an embodiment, computation services 126 include the services or routines, which may be embodied as one or more software agents or computer software routines such as the example embodiments of computer program routines illustratively provided in FIGS. 5 and 6. Computation services 126 also may include services or routines for utilizing one or more prediction, forecasting, or diagnostic models, such as the models described in connection to FIGS. 2A and 2B and the example computer program routines illustratively provided in FIG. 5. In some embodiments, computation services 126 use EHR system(s) 160, model data and model storage services 128, and/or other components of example operating environment 100, and may also include services to facilitate receiving and/or pre-processing physiological data. Model data and model storage services 128 may be utilized to perform services for facilitating storage, retrieval, and implementation of the models described herein and of the data used in the models.

Some embodiments of stack 125 may further comprise services for utilizing an Apache Hadoop and Hbase framework (not shown), or similar frameworks operable for providing a distributed file system, and which in some embodiments facilitate provide access to cloud-based services such as those provided by Cerner Healthe Intent®. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the disclosure also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with ERR system 160. Further, although depicted as a single storage data store, data store 121 may comprise one or more data stores, or may be in the cloud.

Figure 1B:
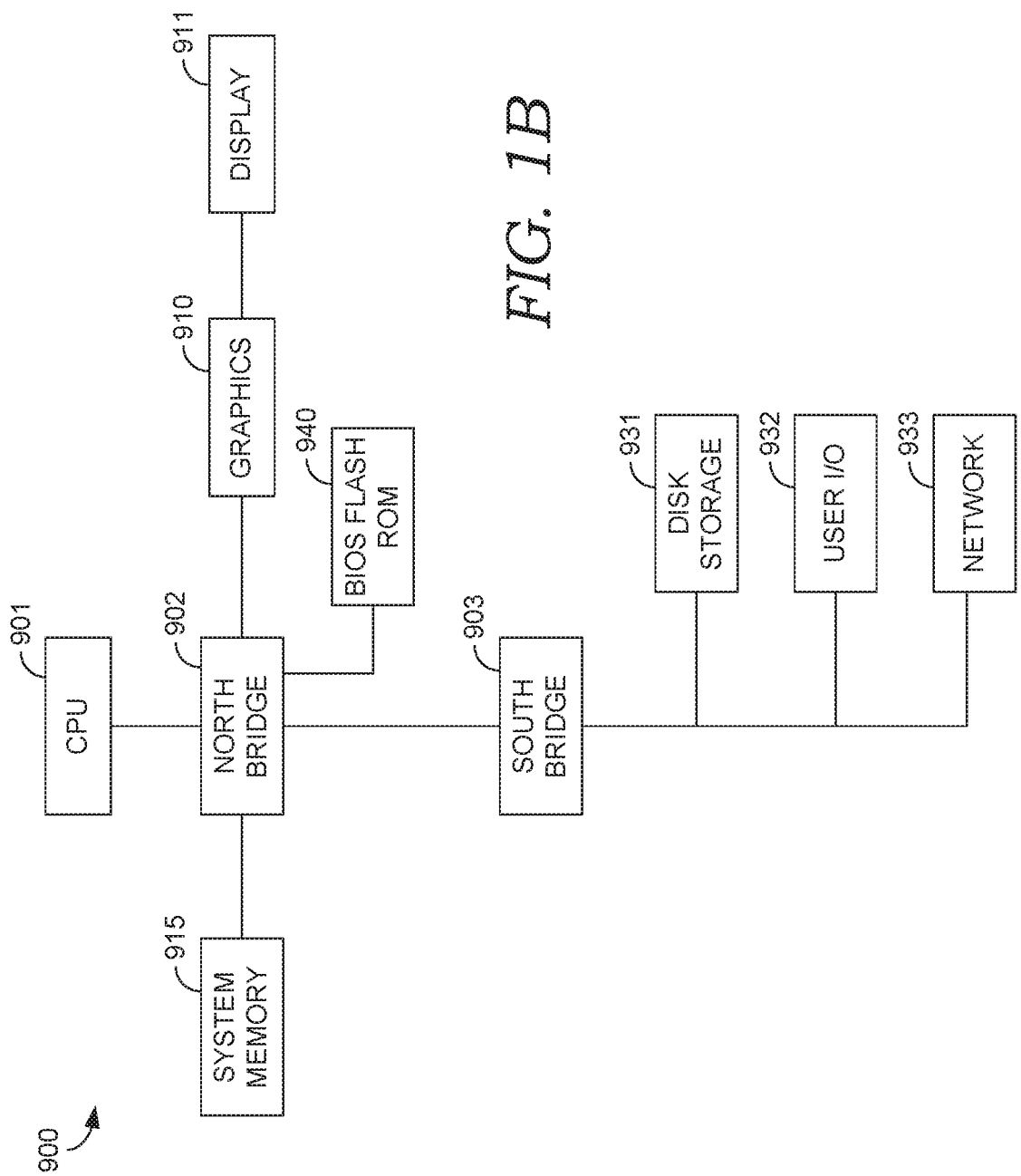

Turning briefly now to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a stylus or touch-stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

In some embodiments, operating environment 100 (or the components of example operating environment 100) include an interface module (or equivalent functionality) for receiving incoming medical data from ERR system(s) 160, a transformation module for transforming the values of input variables referenced in the logistic regression model into intermediate values through dichotomization about a numeric threshold or logical conjunction or sum to totalize individual diagnosis attributions into a composite variable, and a combination module for determining the result of the probability calculation.

Figure 2A:
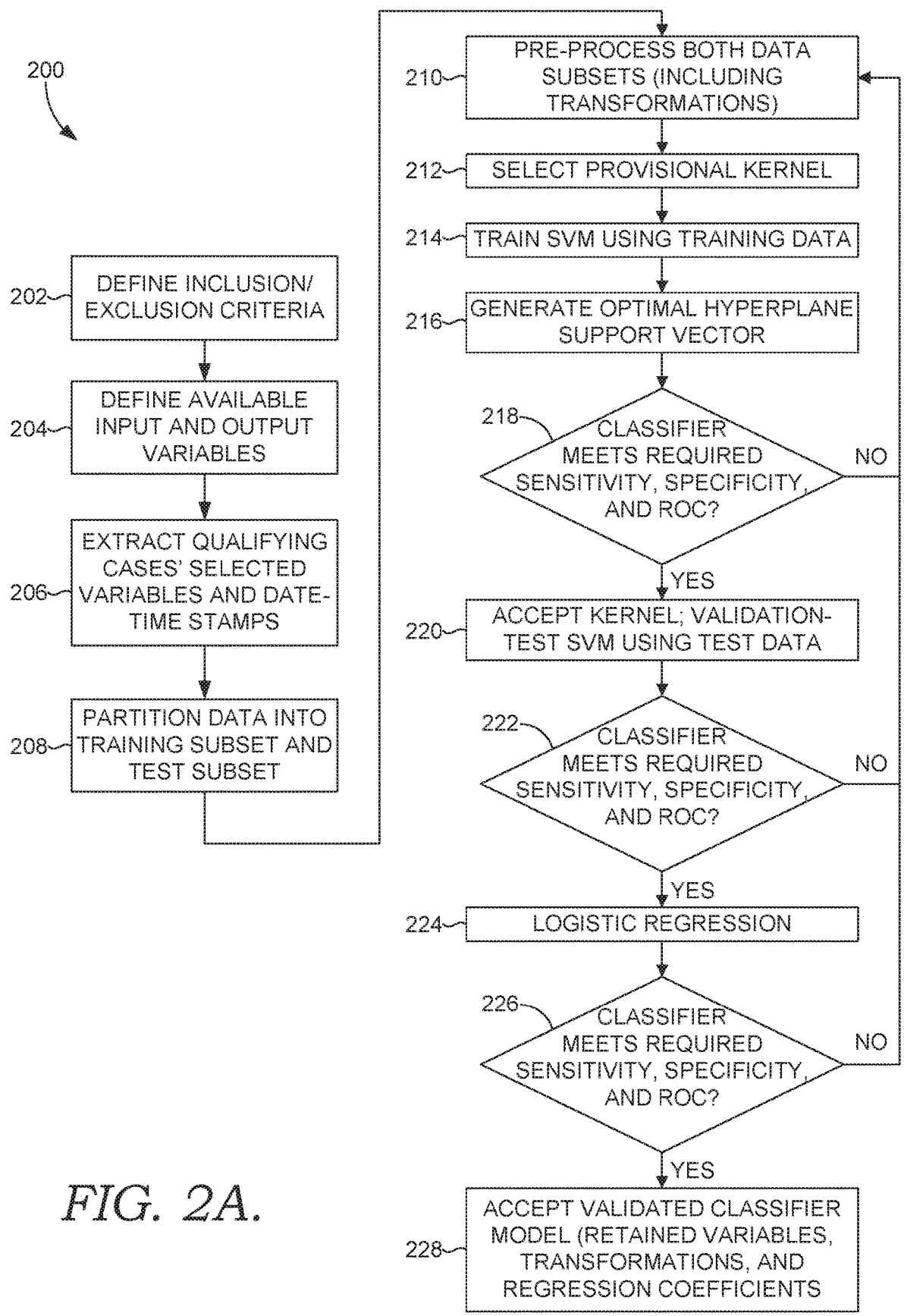
FIG. 2A depicts a flow diagram showing a method for producing and validating a statistical model for accurately predicting a lysosomal storage disorder in accordance with an embodiment of the disclosure.

Turning now to FIG. 2A, a flow diagram is provided that illustrates a method 200 for producing and validating a statistical model for accurately predicting a glycogen storage disease (or condition) in accordance with an embodiment of the technologies described herein. Initially, inclusion-exclusion criteria are defined, as shown at step (or block) 202, as well as problem specification in terms of available input and output variables, at step 204. Thereafter, as shown at step 206, training data is received. Training data comprises a set of data points having known characteristics. This data may come from research facilities, academic institutions, commercial entities, and/or other public or confidential sources. In the case of the present example embodiment, the data came from an anonymized data warehouse of U.S. hospitals' electronic medical record (EMR) data. The collection of training data may be accomplished manually or by way of an automated process, such as known electronic data transfer methods. Accordingly, an example embodiment of the learning machine for use in conjunction with the present disclosure may be implemented in a networked computer environment.

With reference again to step 202, it is known to those practiced in the art that to construct an effective classifier, appropriate inclusion-exclusion criteria may first be defined in sufficient detail that the cases acquired for the purpose of classifier design accurately represent the population to which the classifier is intended to be applied. By way of example only and not limitation, the inclusion criteria include patients having a glycogen storage disease condition. Some criteria for case inclusion in classifier development pertain to the dependent variables or 'outcomes' that are the object of the classification.

With reference again to step 204, for the cohort meeting the applicable inclusion-exclusion criteria, database retrieval of extant EMRs is performed. This serves to define the available input and output clinical and laboratory variables and characterize the descriptive statistics of each variable and assess the degree of "missingness" of information for each variable. In one embodiment, variables whose values are missing at a greater than 20% rate are excluded from subsequent consideration in classifier construction and development. It should be understood that, although database retrieval of EMRs is described, any type of patient medical or health record may be utilized within the various embodiments of the present disclosure (in the context of method 200 or in other contexts of embodiments described herein).

Next, at step 206, information for the qualifying cases for each of the selected variables is extracted from the EMR or other data source, including the date-time stamp for each item. As shown at step 208, the retrieved cases and case information are partitioned into two subsets—a first subset that is to be utilized for classifier construction and training (training data subset), and a second subset that is to be used for classifier validation testing (test data subset). Any of a variety of partitioning methods can be employed such as are well-known to statisticians practiced in the art. Randomized 'bootstrap' sampling without replacement, for example, may be used to insure that the subsets that are generated are not biased with regard to time, source institutions, or other factors. In some embodiments, the partitioning is made into two subsets of equal size (50%-50%). However, there is no requirement that this be the case. The subsets can be of different sizes. In some embodiments, the sample size of each subset is sufficient to achieve a desired 80% or greater statistical power for classification of the cases.

As shown at step 210, statistical pre-processing may be performed, including calculation of mean, median, standard deviation, skewness, and kurtosis for each of the numerical variables and frequency tables for each of the categorical variables. In instances where the statistical distribution of a numerical variable is markedly skewed, then logarithmic or power-law or other transformation of that variable is performed by methods that are well-known to statisticians, so as to produce a distribution for the transformed variable that is symmetrical and more nearly Gaussian in shape than that of the raw variable. The collected training data is optionally pre-processed in order to allow the learning machine to be applied most advantageously toward extraction of the knowledge inherent in the training data. During this preprocessing stage, a variety of different transformations can be performed on the data to enhance its usefulness. Such transformations, examples of which include addition of expert information, spline conversion, logarithmic or power-law transformations, etc., will be readily apparent to those of skill in the art. However, the preprocessing of interest in an embodiment of the present disclosure is the reduction of dimensionality by way of feature selection.

The resulting dataset is processed with a Support Vector Machine (SVM) algorithm and a provisional kernel is selected, as shown at step 212. Some embodiments of method 200 (and method 201, described in FIG. 2B) utilize computation services 126 (FIG. 1), including R System package gkmSVM. An SVM is a specific type of learning machine that implements a specialized algorithm for providing generalization when estimating a multi-dimensional function from a limited collection of data. The training data subset is used to condition the SVM kernel coefficients and generate a support vector (or hyperplane of the variables) at step 216 that optimally distinguishes the cases according to the dependent variable, which in one embodiment is the outcome of a patient being diagnosed with a glycogen storage disease. An SVM may be used in estimating classification functions (e.g., pattern-recognition problems) and real-valued functions (e.g., function approximation problems and regression estimation problems). Those skilled in the art should appreciate that SVMs are capable of processing input data having extremely large dimensionality. However, in some embodiments, pre-processing includes the use of feature selection methods to reduce the dimensionality of feature space.

As shown at step 214, the SVM is trained using the pre-processed data from the training data subset. Accordingly, the SVM is trained by adjusting its operating parameters until a desirable training output is achieved. The determination of whether a training output is desirable may be accomplished by comparing the training output to the known characteristics of the training data. A learning machine is considered to be trained when its training output is within a predetermined error threshold from the known characteristics of the training data.

As is known in the art, different kernels will cause an SVM to produce varying degrees of quality in the output for a given set of input data. Therefore, the selection of an appropriate kernel may be essential to the desired quality of the output of the SVM. In one embodiment of the learning machine, a kernel may be chosen based on prior performance knowledge, such as the relation of various clinical and laboratory variables to symptoms of glycogen storage diseases. Example kernels include polynomial kernels, radial basis function (RBF) classifier kernels, linear kernels, etc. In an alternate embodiment, a customized kernel may be created that is specific to a particular problem or type of data set. The quality of the outputs for each simultaneously trained and tested SVM may be compared using a variety of selectable or weighted metrics to determine whether the kernel chosen performs sufficiently well or whether an alternative kernel achieves superior performance.

At step 218, the resulting classification table is examined by available receiver-operating characteristic (ROC) statistical software, to assess whether the classifier generated by the SVM meets the design requirements established for the predictive model. According to one embodiment, a minimum ROC area-under-the-curve (C-statistic) of 0.80 is required before a model is an acceptable candidate for consideration for logistic regression and subsequent processing and validation. In the event that ROC is lower than the acceptable minimum, then additional iterations of variables selection, pre-processing, kernel generation, and SVM support vector generation are performed (steps 210-218). Alternatively, if ROC is determined to be acceptable at step 218, then the kernel and support vector are accepted and the model is validation-tested, as shown at step 220, using the test data subset that was previously prepared and reserved at step 208. One example ROC for an example embodiment actually constructed using a predictive model generated according to method 200 is illustratively shown in FIG. 4A. Additionally, an example computer program routine for generating the ROC according to method 200 is illustratively provided in FIG. 6.

Figures 4A, 4B:
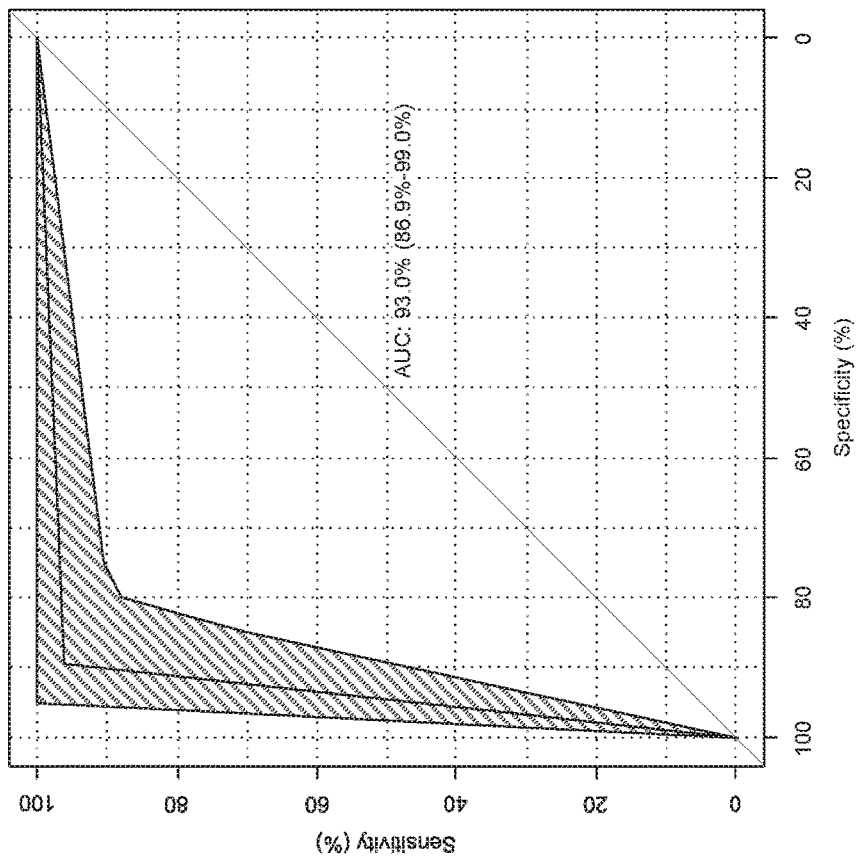
FIGS. 4A and 4B depict aspects of the statistical performance of an example embodiment for predicting a glycogen storage disease that is actually reduced to practice, including a receiver operating characteristic (ROC) curve and statistical performance measures.

Based on the post-processed test output, it is determined at steps 222, 224, and 226 whether an optimal minimum was achieved by the SVM and logistic regression. Those skilled in the art should appreciate that an SVM is able to ascertain an output having a global minimum error. However, as mentioned above, output results of an SVM for a given data set will typically vary with kernel selection. Therefore, there are in fact multiple global minimums that may be ascertained by an SVM for a given set of data. As used herein, the term "optimal minimum" or "optimal solution" refers to a selected global minimum that is considered to be optimal (e.g. the optimal solution for a given set of problem specific, pre-established criteria) when compared to other global minimums ascertained by an SVM. Accordingly, at step 222, determining whether the optimal minimum has been ascertained may involve comparing the output of an SVM with a historical or predetermined value. One example of the statistical performance, which may be assessed in step 222 is shown in FIG. 4B, which includes statistical performance measurements for the example embodiment actually reduced to practice, described above.

If it is determined that the optimal minimum has not been achieved by the trained SVM, the method moves to step 210, and kernel selection is readjusted. Adjustment of the kernel selection may comprise selecting one or more new kernels or adjusting kernel parameters. Furthermore, in the case where multiple SVMs were trained and tested simultaneously, selected kernels may be replaced or modified while other kernels may be re-used for control purposes. After the kernel selection is adjusted, the method is repeated from step 212, where the pre-processed training data is input into the SVM for training purposes. When it is determined at step 222 that the optimal minimum has been achieved, test data is collected in manners similar to those described above. By definition, live data has not been previously evaluated, so that the desired output characteristics that were known with respect to the training data and the test data are not known.

Additional test data is optionally collected in preparation for testing the trained SVM. Test data may be collected from one or more local and/or remote sources. In some embodiments, test data and training data may be collected from the same source(s) at the same time. Thus, test data and training data sets can be divided out of a common data set and stored in a local storage medium for use as different input data sets for a learning machine. Regardless of how the test data is collected, any test data used is pre-processed at step 210 in the same manner as was the training data. As should be apparent to those skilled in the art, a proper test of the learning machine may be accomplished by using testing data of the same format as the training data. Then, at step 220, the learning machine is tested using the pre-processed test data, if any. The test output of the learning machine is optionally post-processed in order to determine if the results are desirable. Again, the post processing step involves interpreting the test output into a meaningful form. The meaningful form may be one that is readily understood by a human or one that is compatible with another processor. Regardless, the test output may be post-processed into a form which may be compared to the test data to determine whether the results were desirable. Examples of post-processing steps include but are not limited of the following: optimal categorization determinations, scaling techniques (linear and non-linear), transformations (linear and non-linear), and probability estimations (such as logit or probit equations).

After validation testing has confirmed a vector of variables and transformations that achieves acceptable sensitivity, specificity, and ROC performance, a logistic regression model is calculated, at step 224, utilizing the input variables and transformations that were developed and validated in the previous steps. The generation of the logistic regression model may be done using the training data subset or the entire original dataset or other partitions derived from it, depending on missing data for some variables or other pragmatic factors. Embodiments of method 200 do not depend upon any particular partitioning at this step. Indeed, the sample size available may often dictate what partitioning is possible, insofar as logistic regression does not tolerate missing data elements. If a decision is made to retain cases that contain missing data in the logistic regression step, then hot-deck or last-value-carry-forward, or other imputation methods may be used, such as are familiar to statisticians.

Finally, the statistical performance of the resulting logistic regression classifier, including its ROC c-statistic, is assessed and, if adequate to the intended purpose, accepted for implementation, as shown at steps 226 and 228. Accepted classifiers may be stored as predictive models utilizing model data and model storage services 128, described in FIG. 1. These predictive models then may be utilized, as described in method 201 (FIG. 2B) for determining presence, identity, and/or severity of a glycogen storage disorder in a patient.

Utilizing method 200, a set of physiological variables were determined for independent model variables. In particular and in some embodiments, these model variables function as a multi-variable composite biomarker and include one or more of: attribution of myalgia; attribution of a plurality (e.g., three or more) specific comorbid conditions; elevated creatine kinase; increased red blood cell size distribution width (RDW; elevated aminotransferases; elevated alanine aminotransferase to aspartate aminotransferase ratio; erythrocyte microcytosis; increased anion gap; and/or laboratory indicia of hypothyroidism. In one embodiment, the specific comorbid conditions include: muscle weakness or sarcopenia; dyspnea or orthopnea; dysphagia; abnormal gait; camptocormia; hypertension; left ventricular hypertrophy; respiratory acidosis; sleep-disordered breathing or obstructive sleep apnea; recurrent community-acquired pneumonia; acute respiratory failure; abdominal pain; diarrhea; bloating; and/or wheelchair dependency as a composite variable.

Figure 2B:
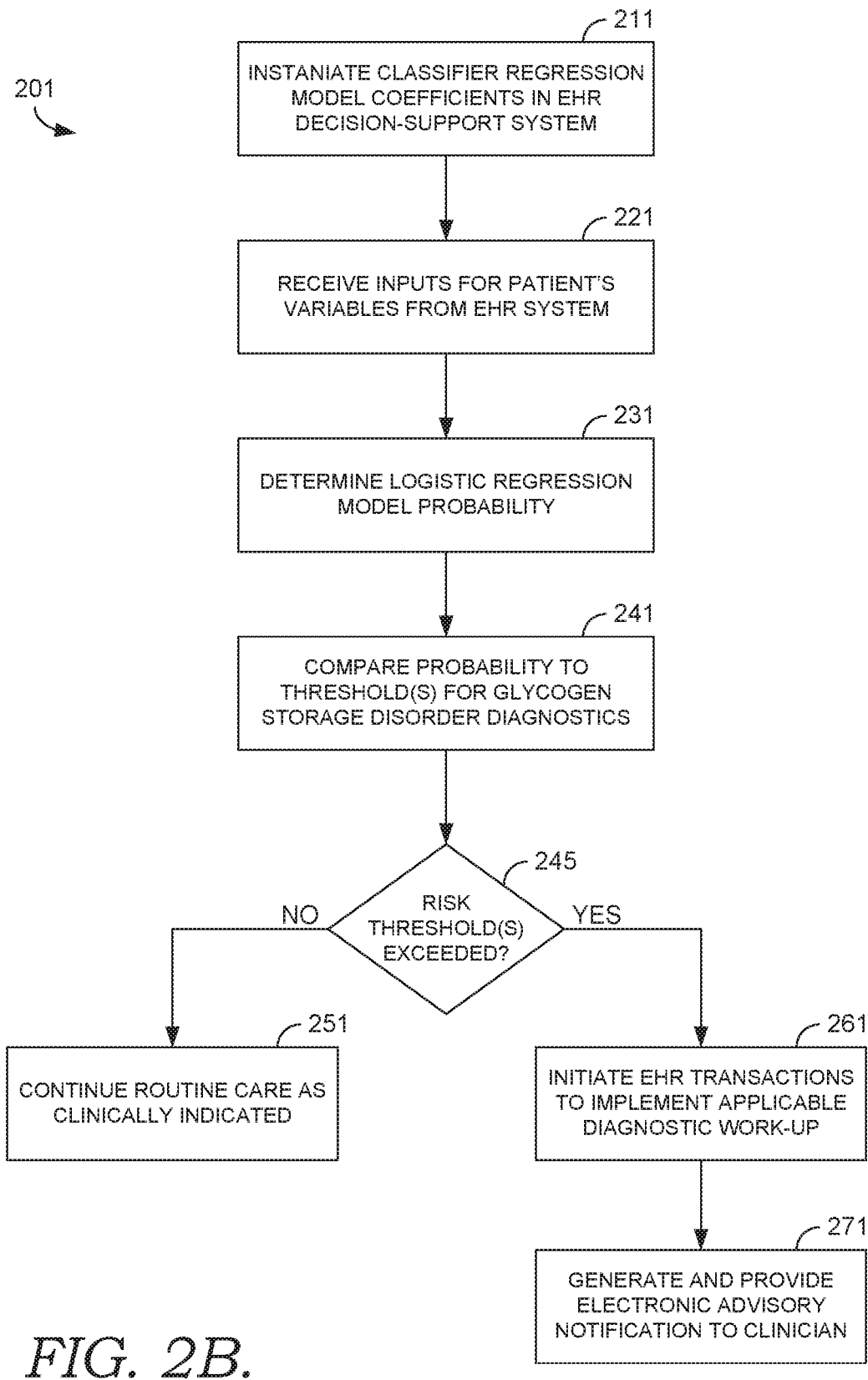
FIG. 2B depicts a flow diagram of an example method for determining presence, identity, and/or severity of a lysosomal storage disorder, such as a glycogen storage disease, using a multi-variable logistic regression statistical model, in accordance with an embodiment of the disclosure.

Turning now to FIG. 2B, a flow diagram is provided illustrating a method 201 for determining presence, identity, and/or severity of a glycogen storage disease or condition using a multi-variable logistic regression statistical model, which may be determined according to method 200 (FIG. 2A). At step 211, instantiate classifier regression model coefficients. Embodiments of step 211 initiate a predictive model having coefficients corresponding to independent model variables. In some embodiments of step 211, the prediction model comprises classifier regression model for classifying likelihood of a patient having a glycogen storage disease or condition and may be determined according to method 200 (FIG. 2A). In some embodiments, the model is generated using a support vector machine, gradient boosting, or other machine-learning means to reduce the initial dimensionality of the statistical analysis. In some instances, the model (or computer-instructions for instantiating the model when called upon) may be incorporated into a decision-support tool for use by a caregiver, such as a health care professional. Some embodiments integrate with other decision support tools and related tools, such as Cerner Millennium® orders, Discern® Expert CDS, iView®, or similar applications.

At step 221, a patient is identified and ERR information for the patient is accessed. The EHR information may include demographic, diagnostic, and laboratory information about the patient. In particular, at step 221, inputs for variable values corresponding to the independent variables of the classifier model may be received from the patient's EHR. At step 231, a logistic regression model probability is determined. In some embodiments, the determined probability may be considered a score denoting the likelihood of the patient's having a glycogen storage disease or condition. Some embodiments of steps 231 may be performed using computation services 126 (described in connection to FIG. 1A). In particular, aspects of method 201 may be carried out using the example computer program provided in FIG. 5.

At step 241, the determined probability or score is compared to one or more thresholds for glycogen storage disorder diagnostics. In some embodiments, the threshold(s) may be predetermined, determined empirically, or based on information about the particular patient, caregiver, or other treatment context (e.g., the treatment venue, role of the caregiver, insurer, or other clinical conditions or events associated with the patient). In some embodiments, step 241 comprises correlating the magnitude of the composite biomarker with the presence, identity, and/or severity of the disease or condition by comparing the probability against a set of thresholds indicating a presence, identity, and/or severity of a disease or condition associated with the patient.

For example, the disease or condition may include a lysosomal storage disease, which may include a glycogen storage disease such as late-onset Pompe's Disease (acid alpha-glucosidase deficiency). In some embodiments, based on the comparison in step 241, one or more risk levels are determined associated with the probability or severity of a lysosomal or glycogen storage disorder in the patient.

At step 245, based on the comparison to the one or more thresholds, if the threshold(s) are not exceeded, then at step 251 routine care for the patient may be carried out, as clinically indicated. But where the one or more thresholds are satisfied, then method 201 proceeds to step 261 and one or more intervening actions may be invoked. In particular, at step 251, additional diagnostics (such as more expensive or time-consuming testing) may be performed on the patient. In addition or in the alternative, other intervening actions may be performed. These actions may be based on the determined probability or score satisfying the threshold(s) or the specific value of the determined probability or score. For example, such actions may comprise generating and providing an electronic notification at step 271 (such as a message or alert) to the patient or a caregiver regarding the determined presence, identity, and/or severity of the glycogen storage disorder in the patient, for instance, a message advising a caregiver of the probability of an inherited acid alpha-glucosidase deficiency meriting further diagnostic testing; generating and providing a specific recommendation regarding the treatment or care of the patient (including recommending diagnostics, courses or care, or additional screenings), and/or automatically performing additional actions such as scheduling diagnostic testing, treatments, modification to care plans, or other intervening actions. In one embodiment, an EHR transaction is initiated to implement applicable diagnostic work-up of additional testing procedures for the patient. In some embodiments, an explanatory analysis may be prepared to accompany the model, for significant values and deviations. Further, in some embodiments, the determined score, severity, specific-condition classifications, and/or any recommended actions may be provided via a graphical user interface such as the example user interface shown in FIG. 3.

Example Reduction to Practice

Turning now to FIG. 3, an application graphical user interface 300 is illustratively provided for an example embodiment actually reduced to practice (described below). In some embodiments, example application interface 300 may be embodied as user/clinician interface 142 and/or decision support application 140, described in connection to FIG. 1. Example application interface 300 may comprise a component of a decision-support tool for predicting a glycogen storage disease in a human patient, based on a multivariable predictive model, such as a model determined according to method 200.

Example application interface 300 includes a set of model variables 310, which comprise independent model variables for the prediction model. The set of variables (or in some embodiments, a subset of these variables) may be utilized according to a process, such as method 201, to determine likelihood and/or severity of a condition and thus function as a multi-variable composite biomarker. In some embodiments, variables 310 comprise one or more physiological variables, which may be a raw physiological variable or comprises an interpretation of a raw physiological data about the patient, such as whether a patient has three or more comorbid conditions (such as those shown at item 340) or whether the patient has an anion gap of greater than 15 mEq/L. Accordingly, example application interface 300 may be used by a clinician for acquisition and/or display of the values of variables that contribute to the biomarker, and for display of the value of the determined biomarker. In some embodiments, the values for physiological variables 310 may be inputted by a clinician and/or may be automatically determined by the patient's EHR data.

In the example application interface 300, for a patient between 10 and 50 years old, to determine likelihood and severity, each physiological variable corresponds to a coefficient as follows: Myalgia (ICD-9: 729.1, ICD-10: M79.1): 1.12; three or more of the listed comorbid conditions: 0.92; CK>200 U/L: 0.81; RDW>14.0 µm: 0.66; RBC sedimentation rate>10 mm/hr: 0.63; AST>40 U/L: 0.56; ALT>45 U/L: 0.51; ALT/AST ratio>1.0: 0.47; MCV<82 fL: 0.34; Anion gap>15 mEq/L: 0.28; T4<5.0 µg/dL—or—fT4<0.8 ng/dL—or—treated with levothyroxine: 0.22; and TSH>10 mU/L—or—treated with levothyroxine: 0.19. Where the physiological variable is not present (including where the interpretation criteria is not satisfied, such as, for instance, where an anion gap is present but not greater than 15 mEq/L, then the coefficient is set to zero.

Example application interface 300 includes a prediction result 320 indicating the patient's likelihood or severity of having the particular condition and thus warranting further testing. In this example, based on the specific values of the model variables 310, the likelihood is determined as "high." Example application interface 300 also includes items 330, 332, and 336. At item 330, a likelihood score is shown (here "69%"). In one embodiment, the likelihood score may be determined using logistic regression as:

$$\frac{e^{(-4.93+0.97[\text{sum of the model variable coefficients}])}}{1 + e^{(-4.93+0.97[\text{sum of the model variable coefficients}])}}$$

Items 332 and 336 comprise an example range corresponding to the likelihood shown at result 320. In this example, item 332 is determined as:

$$\frac{e^{(-4.93+0.71[\text{sum of the model variable coefficients}])}}{1 + e^{(-4.93+0.71[\text{sum of the model variable coefficients}])}}$$

and item 336 is determined as:

$$\frac{e^{(-4.93+1.23[\text{sum of the model variable coefficients}])}}{1 + e^{(-4.93+1.23[\text{sum of the model variable coefficients}])}}$$

Reduction to practice and testing was accomplished using a server cluster (computer system 120) running the Linux operating system (operating system 129), the open-source statistical software package R (software services 126), and the R packages kernlab, caret, and gkmSVM, which were utilized for dimensionality reduction by SVM and gradient boosting methodsm and in particular, using the example computer program routine illustratively depicted in FIG. 5. Initial logistic regression modeling was performed using the glm function in the base R software to produce a regression model that was subjected to a separate validation step.

For the computation of probability or severity of a lysosomal storage disorder: the demographics, laboratory tests, diagnoses, medications, and physical exam records of 3,605 patients having received enzyme-proven diagnosis of late-onset Pompe disease 172 distinct U.S.-based health care institutions between 1 Jan. 2000 and 31 Oct. 2015 were retrieved from a de-identified, secondary-use-consented, EHR-derived, HIPAA-compliant data warehouse (Cerner Health Health Facts® data warehouse). The retrieval encompassed more than 500 laboratory tests, 23 vital signs and flowsheet observation types, and more than 900 medication types as input variables for classification and predictive analysis. Corresponding records for an age-gender matched set of 4,260 control patients incident upon the same 172 institutions during the same time interval were also extracted. A support vector machine (SVM) method, such as described in method 200, was used to identify a subset of the input variables, including 10 laboratory tests, that were statistically significantly associated with the diagnosis of the glycogen storage disease condition (in this specific example actually reduced to practice, the glycogen storage condition is late-onset Pompe disease).

To validate the regression model, records of 29 newly-incident late-onset Pompe disease patients whose care commenced at 13 distinct facilities between 1 Nov. 2015 and 31 Oct. 2016 were retrieved. Corresponding records for 38 age-gender matched control patients incident upon the same 13 institutions during the same time interval were also extracted. Owing to the small number of patients in the validation cohort, conventional logistic regression was not practical and therefore a Markov Chain Monte Carlo (MCMC) Bayesian method (e.g., metrop function in the mcmc R package) was used to perform confirmatory logistic regression. The MCMC Bayesian logistic regression was successful and produced stable results with 1,000 MCMC iterations. Bayes Information Criterion (BIC) and model regression coefficients did not differ significantly from the initial model. FIGS. 4A and 4B depict aspects of the statistical performance of this example embodiment actually reduced to practice using this clinical dataset, including a ROC curve (FIG. 4A) and statistical performance measures (FIG. 4B).

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure. For instance, some example alternative embodiments include:

Embodiment 1: One or more computer-readable storage devices storing computer-useable instructions that, when used by one or more computing devices, cause the one or more computing devices to perform a method comprising: identifying an EMR associated with a human patient; generating a multi-variable logistic regression statistical model capable of calculating a probability of a clinically significant glycogen storage disease; receiving input data from the medical record for the human patient; determining from the received input data set a multi-variable biomarker based on a set of physiological variables in the received input data comprising a plurality of: attribution of myalgia, attribution of a plurality of comorbid conditions, elevated creatine kinase, increased red blood cell size distribution width (RDW), elevated aminotransferases, elevated alanine aminotransferase to aspartate aminotransferase ratio, erythrocyte microcytosis, increased anion gap, and/or laboratory indicia of hypothyroidism; determining a probability of the clinically significant glycogen storage disease for the human patient based on the multi-variable biomarker and the multi-variable logistic regression statistical model; modifying the EMR according to the determined probability and to include data indicating that the member associated with the medical record is a candidate for receiving additional treatment or diagnostic procedures associated with glycogen storage disorders; and based on the probability of clinically significant glycogen storage disease for the human patient, determined from the multi-variable biomarker and the multi-variable logistic regression statistical model, initiating an intervention action, the intervention action comprising one or more of modifying treatment of the patient, ordering additional diagnostics for the patient, scheduling treatment or diagnostics for the patient, and issuing a notification to a caregiver associated with the patient, wherein multi-variable biomarker is used by the multi-variable logistic regression statistical model.

Embodiment 2: Embodiment 1, wherein a plurality of comorbid conditions includes at least three comorbid conditions.

Embodiment 3: Any of Embodiments 1-2, wherein the comorbid conditions include: muscle weakness or sarcopenia, dyspnea or orthopnea, dysphagia, abnormal gait, camptocormia, hypertension, left ventricular hypertrophy, respiratory acidosis, sleep-disordered breathing or obstructive sleep apnea, recurrent community-acquired pneumonia, acute respiratory failure, abdominal pain, diarrhea, bloating, and wheelchair dependency as a composite variable.

Embodiment 4: A method of determining the presence, identity, and/or severity of a lysosomal storage disease or condition in an individual, where the disease or condition is associated with abnormal glycan or glycogen degradation or accumulation, the method comprising: (a) generating a biomarker as a probability or score emitted by a logistic regression model, wherein the independent variables referenced in said logistic regression model comprise: attribution of myalgia, attribution of a plurality of the conditions muscle weakness or sarcopenia, dyspnea or orthopnea, dysphagia, abnormal gait, camptocormia, hypertension, left ventricular hypertrophy, respiratory acidosis, sleep-disordered breathing or obstructive sleep apnea, recurrent community-acquired pneumonia, acute respiratory failure, abdominal pain, diarrhea, bloating, or wheelchair dependency as a composite variable, elevated creatine kinase, increased red blood cell size distribution width (RDW), elevated aminotransferases, elevated alanine aminotransferase to aspartate aminotransferase ratio, erythrocyte microcytosis, increased anion gap, and/or laboratory indicia of hypothyroidism; and (b) correlating the magnitude of the biomarker with the presence, identity, and/or severity of the disease or condition for determining the presence, identity, and/or severity of the disease or condition; wherein the disease or condition is a lysosomal storage disease; wherein when the lysosomal storage disease is a glycogen storage disease; and wherein the glycogen storage disease is late-onset Pompe's Disease (acid alpha-glucosidase deficiency).

Embodiment 5: Embodiment 4, wherein the multi-variable logistic regression statistical model is generated using a support vector machine, gradient boosting, or other machine-learning means to reduce the initial dimensionality of the statistical analysis.

Embodiment 6: Any of Embodiments 4-5, wherein the method further comprises determining one or more risk levels associated with the probability or severity of the lysosomal storage disorder in a human patient.

Embodiment 7: Any of Embodiments 4-6, wherein the method further comprises communicating for presentation to a clinician the one or more risk levels.

Embodiment 8: Any of Embodiments 4-7, wherein the method further includes communicating the EMR to a clinician, where EMR indicates the probability or severity of the lysosomal storage disorder in a human patient.

Embodiment 9: A method for screening for the presence, identity, and/or severity of a lysosomal storage disorder in a human patient, comprising: generating a multi-variable logistic regression statistical model capable of calculating a probability or severity of said lysosomal storage disorder using a plurality of variables; receiving an input data set for a human patient based on laboratory test results for the patient, the data set including a time associated with the test results, the test results determined from measurements that may be received at multiple measurement-session times; determining a probability or severity of said lysosomal storage disorder based on the input data set and the multi-variable logistic regression statistical model: modifying an EMR associated with the patient according to the determined probability indicating that the patient is or is not a candidate for additional diagnostic testing and treatment; and based on the probability or severity of said lysosomal storage disorder for the human patient determined from the input data set and the multi-variable logistic regression statistical model, initiating an intervention, the intervention comprising undertaking additional diagnostic or prognostic enzymatic or genetic testing directed to one or more specific lysosomal storage disorders.

Embodiment 10: Embodiment 9, wherein the multi-variable logistic regression statistical model is generated using a support vector machine, gradient boosting, or other machine-learning means to reduce the initial dimensionality of the statistical analysis.

Embodiment 11: Any of Embodiments 9-10, wherein the method further comprises determining one or more risk levels associated with the probability or severity of said lysosomal storage disorder.

Embodiment 12: Any of Embodiments 9-11, wherein the method further comprises communicating for presentation to a clinician the one or more risk levels.

Embodiment 13: Any of Embodiments 9-12, further comprising communicating the EMR to a clinician, where EMR indicates the probability or severity of said lysosomal storage disorder.

Embodiment 14: Any of Embodiments 9-13, wherein the probability comprises a multi-variable predictive score calculated using the multi-variable logistic regression statistical model, therein the multi-variable logistic regression statistical model is capable of calculating a probability or severity of said lysosomal storage disorder.

Embodiment 15: Any of Embodiments 9-14, wherein the multi-variable logistic regression statistical model employs a multi-variable support vector machine, gradient boosting, or other machine-learning means to reduce the initial dimensionality of the statistical analysis.

Embodiment 16: Any of Embodiments 9-15, wherein one or more risk levels are identified based on the probability or severity of said lysosomal storage disorder.

Embodiment 17: Any of Embodiments 9-16, wherein the one or more risk levels are presented to a clinician via an EMR software system or device.

Embodiment 18: Any of Embodiments 9-17, wherein the intervention is identified based on the one or more risk levels.

Embodiment 19: A method of determining the presence, identity, and/or severity of a lysosomal storage disease or condition in an individual, implemented in an electronic medical software system, the method comprising: identifying an EMR associated with each member of a set of members of the population who exhibit an above-threshold value of a multi-variable predictive score, the value of the multi-variable predictive score being calculated from a multi-variable logistic regression statistical model and a plurality of variables determined at least in part from laboratory test results from a single set of measurements measured at a known time following birth, and including the known time following birth of the measured test results; and modifying the EMR with data indicating that the member associated with the medical record is a candidate for intervention; and based on the value of the multivariable predictive score, initiating a diagnostic or therapeutic intervention.

Embodiment 20: Embodiment 19, wherein the multi-variable predictive score is calculated using the multi-variable logistic regression statistical model, therein the multi-variable logistic regression statistical model is capable of calculating a probability or severity of said lysosomal storage disorder.

Embodiment 21: Any of Embodiments 19-20, wherein the multi-variable logistic regression statistical model employs a multi-variable support vector machine, gradient boosting, or other machine-learning means to reduce the initial dimensionality of the statistical analysis.

Embodiment 22: Any of Embodiments 19-21, wherein one or more risk levels are identified based on the probability or severity of said lysosomal storage disorder.

Embodiment 23: Any of Embodiments 19-22, wherein the one or more risk levels are presented to a clinician via an EMR software system or device.

Embodiment 24: Any of Embodiments 19-23, wherein the intervention is identified based on the one or more risk levels.

It will be understood that certain features and subcombinations are of utility and may be employed without reference to other features and subcombinations and are contemplated within the scope of the claims. Not all steps listed in the various figures need be carried out in the specific order described. Accordingly, the scope of the disclosure is intended to be limited only by the following claims.

What is claimed is:

1. A computerized method of initiating an electronic health record (EHR) intervention action for glycogen storage disease, the method comprising:

determining a multi-variable biomarker based on a set of physiological variables associated with an individual that is received as input data, the multi-variable biomarker comprising a plurality of: attribution of myalgia, attribution of a plurality of comorbid conditions, elevated creatine kinase, increased red blood cell size distribution width (RDW), elevated aminotransferases, elevated alanine aminotransferase to aspartate aminotransferase ratio, erythrocyte microcytosis, increased anion gap, or laboratory indicia of hypothyroidism;

training a multi-variable logistic regression statistical model to determine a probability of a clinically significant glycogen storage disease, the multi-variable logistic regression statistical model being trained with data from an anonymized data warehouse of electronic medical record (EMR) data that is collected via an automated process;

utilizing the trained multi-variable logistic regression statistical model, determining the probability of the clinically significant glycogen storage disease for the individual based on the multi-variable biomarker; and based on the probability of the clinically significant glycogen storage disease for the individual, automatically initiating the EHR intervention action, wherein the intervention action comprises one or more of modifying treatment of the patient, ordering additional diagnostics for the patient, scheduling treatment or diagnostics for the patient, and issuing a notification to a caregiver associated with the patient.

2. The method of claim 1, wherein the plurality of comorbid conditions includes at least three comorbid conditions selected from: muscle weakness or sarcopenia, dyspnea or orthopnea, dysphagia, abnormal gait, camptocormia, hypertension, left ventricular hypertrophy, respiratory acidosis, sleep-disordered breathing or obstructive sleep apnea, recurrent community-acquired pneumonia, acute respiratory failure, abdominal pain, diarrhea, bloating, and wheelchair dependency.

3. The method of claim 1, wherein the multi-variable logistic regression statistical model is generated using a machine learning technique, and wherein the machine learning technique is support vector machine or gradient boosting.

4. The method of claim 1, further comprising comparing the probability of the clinically significant glycogen storage disease to a diagnostic threshold, wherein the diagnostic threshold is part of a set of diagnostic thresholds that indicate a presence, identity, or severity of the probability of the clinically significant glycogen storage disease, and wherein automatically initiating the EHR intervention action is further based on comparing the probability to the diagnostic threshold.

5. The method of claim 1, wherein the input data is received from an EMR associated with the individual.

6. One or more computer-readable storage devices storing computer-useable instructions that, when used by one or more computing devices, cause the one or more computing devices to perform a method of initiating an electronic health record (EHR) intervention action for glycogen storage disease, the method comprising:

determining a multi-variable biomarker based on a set of physiological variables associated with an individual that is received as input data, the multi-variable biomarker comprising a plurality of: attribution of myalgia, attribution of a plurality of comorbid conditions, elevated creatine kinase, increased red blood cell size distribution width (RDW), elevated aminotransferases, elevated alanine aminotransferase to aspartate aminotransferase ratio, erythrocyte microcytosis, increased anion gap, or laboratory indicia of hypothyroidism;

training a multi-variable logistic regression statistical model to determine a probability of a clinically significant glycogen storage disease, the multi-variable logistic regression statistical model being trained with data from an anonymized data warehouse of electronic medical record (EMR) data that is collected via an automated process;

utilizing the trained multi-variable logistic regression statistical model, determining the probability of the clinically significant glycogen storage disease for the individual based on the multi-variable biomarker; and based on the probability of the clinically significant glycogen storage disease for the individual, automatically initiating the EHR intervention action, wherein the intervention action comprises one or more of modifying treatment of the patient, ordering additional diagnostics for the patient, scheduling treatment or diagnostics for the patient, and issuing a notification to a caregiver associated with the patient.

7. The one or more computer-readable storage devices of claim 6, wherein the multi-variable logistic regression statistical model is generated using a machine learning technique.

8. The one or more computer-readable storage devices of claim 7, wherein the machine learning technique is support vector machine or gradient boosting.

9. The one or more computer-readable storage devices of claim 6, further comprising comparing the probability of the clinically significant glycogen storage disease to a diagnostic threshold, wherein the diagnostic threshold is part of a set of diagnostic thresholds that indicate a presence, identity, or severity of the clinically significant glycogen storage disease.

10. The one or more computer-readable storage devices of claim 9, wherein automatically initiating the EHR intervention action is further based on comparing the probability to the diagnostic threshold.

11. The one or more computer-readable storage devices of claim 6, further comprising determining a risk level of the clinically significant glycogen storage disease based on comparing the probability to the diagnostic threshold, and communicating the risk level as part of the notification.

12. The one or more computer-readable storage devices of claim 6, wherein the input data is received from an EMR associated with the individual.

13. One or more computer-readable storage devices storing computer-useable instructions that, when used by one or more computing devices, cause the one or more computing devices to perform a method of initiating an electronic health record (EHR) intervention action for glycogen storage disease, the method comprising:

identifying an EMR associated with an individual;

training a multi-variable logistic regression statistical model to determine a probability of a clinically significant glycogen storage disease, the multi-variable logistic regression statistical model being trained with data from an anonymized data warehouse of electronic medical record (EMR) data that is collected via an automated process;

receiving input data from the EMR associated with the individual;

determining a multi-variable biomarker based on a set of physiological variables in the received input data, the multi-variable biomarker comprising a plurality of: attribution of myalgia, attribution of a plurality of comorbid conditions, elevated creatine kinase, increased red blood cell size distribution width (RDW), elevated aminotransferases, elevated alanine aminotransferase to aspartate aminotransferase ratio, erythrocyte microcytosis, increased anion gap, or laboratory indicia of hypothyroidism;

utilizing the trained multi-variable logistic regression statistical model, determining the probability of the clinically significant glycogen storage disease for the individual based on the multi-variable biomarker; and based on the probability of the clinically significant glycogen storage disease for the individual, automatically initiating the EHR intervention action, wherein the intervention action comprises one or more of modifying treatment of the patient, ordering additional diagnostics for the patient, scheduling treatment or diagnostics for the patient, and issuing a notification to a caregiver associated with the patient.

14. The one or more computer-readable storage devices of claim 13, further comprising modifying the EMR according to the determined probability to include data indicating that the individual associated with the EMR is a candidate for receiving additional treatment or diagnostic procedures associated with the clinically significant glycogen storage disease.

15. The one or more computer-readable storage devices of claim 13, further comprising comparing the probability of the clinically significant glycogen storage disease to a diagnostic threshold.

16. The one or more computer-readable storage devices of claim 15, wherein the diagnostic threshold is part of a set of thresholds that indicate a presence, identity, or severity of the clinically significant glycogen storage disease.

17. The one or more computer-readable storage devices of claim 13, further comprising determining a risk level of the clinically significant glycogen storage disease based on comparing the probability to the diagnostic threshold, and communicating the risk level as part of the notification.

18. The one or more computer-readable storage devices of claim 13, wherein automatically initiating the EHR intervention action is further based on comparing the probability to the diagnostic threshold.

19. The one or more computer-readable storage devices of claim 13, wherein the plurality of comorbid conditions includes at least three comorbid conditions.

20. The one or more computer-readable storage devices of claim 19, wherein the plurality of comorbid conditions includes at least three comorbid conditions selected from: muscle weakness or sarcopenia, dyspnea or orthopnea, dysphagia, abnormal gait, camptocormia, hypertension, left ventricular hypertrophy, respiratory acidosis, sleep-disordered breathing or obstructive sleep apnea, recurrent community-acquired pneumonia, acute respiratory failure, abdominal pain, diarrhea, bloating, and wheelchair dependency as a composite variable.

* * * * *